United States Patent [19]

Boudjouk et al.

[11] Patent Number: 4,466,870

[45] Date of Patent: Aug. 21, 1984

[54] ORGANIC SONOCHEMISTRY PROCESS

[75] Inventors: Philip R. Boudjouk; Byung-Hee Han, both of Fargo, N. Dak.

[73] Assignee: North Dakota State University Development Foundation, Fargo, N. Dak.

[21] Appl. No.: 443,577

[22] Filed: Nov. 22, 1982

[51] Int. Cl.$^3$ .............................................. B01J 19/10
[52] U.S. Cl. .............................. 204/158 S; 204/162 S
[58] Field of Search .......................... 204/158 S, 162 S

[56] References Cited

U.S. PATENT DOCUMENTS 3,128,240 4/1964 Kusy ................................. 204/162 S
3,630,866 12/1971 Pelofsky ........................... 204/162 S
3,833,491 9/1974 Kennedy .......................... 204/162 S Primary Examiner—Howard S. Williams

[57] ABSTRACT

The method of causing or promoting chemical changes involving the step of subjecting reactants to ultrasonic energy as a key treatment step, including methods of: (1) reducing aryl halides by treating a mixture of aryl halide and lithium aluminum hydride in a liquid ether medium; (2) making cycloaddition products by treating a mixture of alpha, alpha'-dibromo-ortho-xylene, zinc powder and a dienophile in a liquid ether medium; (3) making beta-hydroxyesters by treating a mixture of alpha-bromoethylacetate, a carbonyl compound, zinc dust and an iodine enhancer in a liquid ether medium; (4) making tetramesityldisilene involving treating a solution of bis(mesityl)dichlorosilane in a liquid ether medium, with lithium present in the medium; and (5) saturating organic compounds having capability of reduction at carbon-carbon bonds involving treating a mixture of an organic compound having capability of reduction at carbon-carbon bonds, and formic acid, in an alcohol medium with palladium-on-carbon present as a catalyst.

7 Claims, No Drawings

ORGANIC SONOCHEMISTRY PROCESS

This invention relates to organic sonochemistry, namely ultrasonically caused or promoted chemical changes, and more particularly relates to areas of organic sonochemistry involving: (1) reducing aryl halides; (2) making cycloaddition products; (3) making beta-hydroxyesters; (4) making tetramesityldisilene; and (5) saturating organic compounds having capability of reduction at carbon-carbon bonds.

The invention is useful in formulating products of commerce, in organic synthesis, and in other more specific ways outlined below.

In some cases the reaction occurs to some extent without ultrasonic treatment; but ultrasonic treatment accelerates the reaction or promotes more complete reaction under conditions making commercial adoption practical. In a few cases, reaction is effectively caused by ultrasonic treatment; without it there was no significant evidence of reaction.

Useful ranges of frequency for ultrasonic energy treatment according to the invention may vary. As a practical matter, the frequency and waves of an ultrasonic source may include some that are in the audible range; but those are not considered significant. The most useful frequencies are those at least approaching about 50 kHz, preferably with a concentration or a majority between about 50 and 60 kHz. Most experiments were conducted with the major concentration approximately 55 kHz; but deviation away from this concentration can produce useful results. Extremely simple apparatus may be employed as the generator or source for ultrasonic energy, e.g., a common ultrasonic cleaner for laboratory equipment.

(1) Reducing Aryl Halides

This embodiment is particularly useful for reducing the toxicity or detoxifying halogenated pesticides. In addition it is useful in organic synthesis where removal of halogen is an important part of the process. The embodiment also has value as a way to form solvents useful in commercial applications.

The embodiment provides a method for reducing aryl halides involving nucleophilic substitution of hydrogen for halide on the aryl nucleus, comprising forming a mixture of aryl halide and lithium aluminum hydride in a liquid ether medium (e.g., in dimethoxyethane), and subjecting the mixture to ultrasonic energy.

Further details of this embodiment, including examples of it, are set forth in a paper entitled "ORGANIC SONOCHEMISTRY. ULTRASONIC ACCELERATION OF THE REDUCTION OF SIMPLE AND DEACTIVATED ARYL HALIDES USING LITHIUM ALUMINUM HYDRIDE", which we wrote and which was published heretofore in 1982 in Tetrahedron Letters, Vol. 23, No. 16, pp. 1643–1646, pertinent portions of which will now be set forth as part of this specification.

That aromatic halides are reluctant substrates for nucleophilic substitution is well-known and it is generally accepted that electron-donating groups on the ring further impede displacement of the halogen. Nucleophilic hydrogen, however, in the form of complex metal hydrides, has been employed with some success in the reduction of aryl halides. Bromobenzene, for example, gave a 52% yield of benzene after 6 h and 95% after 24 h when treated with a four molar excess of a tetrahydrofuran (THF) solution of LiAlH$_4$. However, deactivated halides, like p-bromoanisole and p-bromotoluene, for example, produced only a 17% yield of anisole and a 20% yield of toluene, respectively under the same conditions.

We have found that sonic acceleration can be applied to these systems and in this communication we report our preliminary results on the lithium aluminum hydride reductions of some simple and deactivated aryl halides. Our results are summarized in the Table.

TABLE $$Ar-X + LiAlH_4 \xrightarrow{))))} Ar-H$$

Ultrasound-Accelerated Reductions of Aromatic Halides

| | Ar—X | Ar—H | Yield (time, h)$^a$ | Comparison (yield; time; temp.; solvent)$^b$ |
|---|---|---|---|---|
| 1. | o-Bromotoluene | Toluene | 98% (5h) | 21%; 24h; 25°, THF |
| 2. | p-Bromotoluene | Toluene | 97% (5h) | 20%; 24h; 25°, THF |
| 3. | m-Bromotoluene | Toluene | 81% (6h) | |
| 4. | o-Iodotoluene | Toluene | 95% (5h) | 92%; 24h; 100°; Diglyme |
| 5. | o-Bromoanisole | Anisole | 98% (4h) | 58%; 24h; 100°; Diglyme |
| 6. | p-Bromoanisole | Anisole | 70% (7h) | 35%; 24h; 100°; Diglyme |
| 7. | p-Iodoanisole | Anisole | 73% (7h) | 91%; 24h; 100°; Diglyme |
| 8. | 1-Bromonaphthalene | Naphthalene | 99% (6h) | 99%; 6h; 65°; THF |
| 9. | 1-Iodonaphthalene | Naphthalene | 99% (6h) | 72%; 24h; 65°; THF |
| 10. | 1-Chloro-3-bromobenzene | Chlorobenzene | 98% (4h)$^c$ | 95%; 24h; 25°; THF |
| 11. | 1-Chloro-4-bromobenzene | Chlorobenzene | 98% (4h)$^c$ | |

$^a$All of our reactions were run at 35° in dimethoxyethane using a 1:1 molar ratio of LiAlH$_4$:ArX.
$^b$A 1:1 ratio of LiAlH$_4$:ArX was employed in all cases except comparison examples 8 and 10 which required ratios of 4:1 and 1.5:1 respectively.
$^c$Traces of benzene were also observed by nmr.

Improvements in yields or reaction conditions are significant in all cases but the most dramatic differences are those observed for the deactivated halides. In a typical experiment, 10 mmol of an aromatic halide and 10 mmol of LiAlH$_4$ were added to 10 ml of dry THF. The reaction mixture, contained in a 100 ml round bottom single neck flask and maintained under a nitrogen atmosphere, was partly submerged in a common ultrasound laboratory cleaner (117 v, 150 w, 50/60 Hz). Cavitation produced a turbid reaction mixture immediately and after several hours the reaction was quenched and the products isolated.

In each case the workup procedure was the same. The product mixture was first poured slowly onto an ice-CH$_2$Cl$_2$ slurry with stirring. This was extracted twice with CH$_2$Cl$_2$ and the extracts were dried over MgSO4. The solvents were removed by distillation or flash evaporation. Typically the recovery of ArX and ArH exceeded 90%. Yields were obtained by nmr analysis of the product mixture following these steps. Mole ratios of solvent:product:starting material were measured by nmr and used to compute mass balances. Our reaction conditions were not optimized and these reductions may be more efficient than indicated. The literature examples however, are optimized reactions.

There are significant differences in the manner in which our reductions were carried out compared to those by Brown and Krishnamurthy. Our reactions were run as heterogeneous mixtures whereas the comparison examples were THF solutions. This is in concert with earlier observations that heterogeneous reactions benefit greatly from sonication. Also, our solvent was DME which was far more effective than THF in the presence of sonic waves. The functions of surface and solvent in sonically accelerated reactions are not clearly understood and work is now in progress to elucidate the roles of these variables in the ArX→ArH transformation. Additionally, we are investigating other complex hydrides to determine if they can be activated by sound as well as broadening the scope of the LiAlH4/DME reducing system to other substrates.

Thus ends the pertinent portions from our aforenoted paper entitled "Organic Sonochemistry. Ultrasonic Acceleration of the Reduction of Simple and Deactivated Aryl Halides Using Lithium Aluminum Hydride."

(2) Making Cycloaddition Products

This embodiment is particularly useful in synthesizing intermediates important to the drug industry, such as those containing an anthracene nucleus (e.g., anthracycline antibiotics). A new use of possibly equal or greater importance is that for the formation of intermediates in the making or manufacture of organic metals such as tetrathiatetracene and its selenium and tellurium analogs.

The embodiment provides a method of making cycloaddition products comprising forming a mixture of alpha, alpha'-dibromo-ortho-xylene, zinc powder and a dienophile in a liquid ether medium (e.g., dioxane), and subjecting the mixture to ultrasonic energy.

Further details of this embodiment, including examples of it, are set forth in a paper entitled "Organic Sonochemistry. Ultrasound-Promoted Reaction of Zinc With alpha, alpha'-Dibromo-ortho-Xylene. Evidence for Facile Generation of alpha-Xylylene", which we wrote and which was published heretofore in 1982 in the Journal of Organic Chemistry, Vol. 47 at page 751, pertinent portions of which will now be set forth as part of this specification.

Summary: α, α'-Dibromo- o-xylene and zinc powder react smoothly in the presence of dienophiles and sonic waves to give high yields of cycloaddition products. The reaction is believed to proceed via the reactive intermediate, o-xylylene.

The effects of ultrasounds on the rates of chemical reactions have been of general interest. In most cases, modest rate enhancements have been the major benefit from using sonic waves although the number of examples of synthetically useful applications is increasing. Recent communications describing an improved modification of the Barbier reaction, a facile reduction of α, α'-dibromo ketones, coupling of organic and organometallic halides, and a new procedure for making thioamides indicate considerable potential for ultrasound in synthesis. We have extended our investigations to organic dihalides and in this communication we report preliminary results of our studies of ultrasonically induced reactions of zinc powder with α, α'-dibromo-o-xylene (1).

We have found that ultrasound accelerates the reaction between zinc and 1 in dioxane, forming high yields of cycloaddition products when dienophiles are present in the reaction mixture. These results are summarized in Table I. No reaction occurs in the absence of ultrasound.

TABLE I
Ultrasound-Induced Reaction of Zinc and α,α'-Dibromo-o-xylene in the Presence of Dienophiles

| dienophile | time, h | product | isolated yield, % |
|---|---|---|---|
| 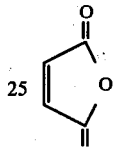 | 15 | 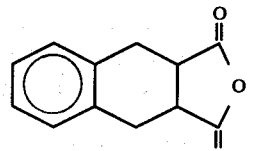 | 89 |
| 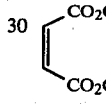 | 12 | 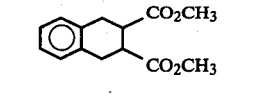 | 70 |
| CH2=CHCO2CH3 | 12 | 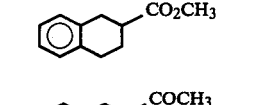 | 67 |
| CH2=CHCOCH3 | 12 | 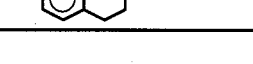 | 87 |

When a dioxane solution of 1 is treated with zinc and ultrasound in the absence of a reactive species, all of 1 is consumed, giving mostly polymer and small quantities (<5% by NMR) of bibenzo[a,e]-6,7,11,12-tetrahydrocyclooctadiene (3). These observations are consistent with the formation of o-xylylene (2) as an important intermediate in these reactions.

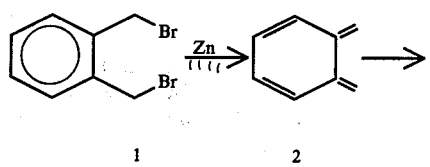

1      2

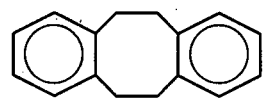

3

Attempts to trap an ionic intermediate like 4 with trimethylchlorosilane were unsuccessful. However, some 3 was detected by NMR.

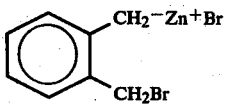

In a typical experiment, 10 mmol of 1, 11 mmol of dienophile, and 23 mmol of activated zinc were added to 10 mL of peroxide-free dioxane freshly distilled from KOH. The reaction mixture, contained in a 25-mL, round-bottom, single-neck flask under an atmosphere of nitrogen, was partly submerged in a common ultrasound laboratory cleaner (117V, 150W, 50/60 Hz). Both temperatures were maintained at 20°-25° C. by using a cooling coil.

Product isolation was straightforward: filtration of the crude product mixture to remove zinc bromide and excess zinc, addition of the filtrate to 20 mL of saturated aqueous ammonium chloride, extraction with methylene chloride and chromatography of the dried solution ($CaCl_2$) on a short neutral alumina column, using methylene chloride as eluant. Chromatography was not necessary for the maleic anhydride adduct. Evaporation of $CH_2Cl_2$ after extraction gave an analytically pure sample. The other adducts were >95% pure (by NMR and GC) following chromatography. Our yields are based on quantities obtained after this step. Analytically pure samples were obtained by preparative gas chromatography. Structural assignments are based on NMR, IR, and mass spectral data and elemental analyses. The cis configuration of the product from the reaction of dimethyl maleate was assigned because it was the only product from that reaction and it was different from the single product obtained when dimethyl fumarate was used as the dienophile.

The production of 2 is strongly implied by these observations and, if so, ultrasound provides a convenient low-temperature route to this intermediate. That 1 is commercially available and inexpensive makes this procedure very attractive. Typically 2 is generated in synthetically useful quantities at high temperatures from intermediates requiring one or two synthetic steps. Work is now in progress to broaden the scope of the reactions of 2 as well as to apply this technique to vicinal and geminal dihalides.

This ends the pertinent portions from our aforenoted paper entitled "Organic Sonochemistry. Ultrasound-Promoted Reaction of Zinc with alpha, alpha'-Dibromo-ortho-Xylene."

(3) Making beta-Hydroxyesters

Besides being generally useful to make alpha beta unsaturated esters having many known usages in industry, this embodiment, involving the Reformatsky Reaction, is highly useful in the drug industry for the synthesis or manufacture of intermediates.

The embodiment provides a method of making beta-hydroxyesters comprising forming a mixture of alpha-bromoethylacetate, a carbonyl compound, zinc dust, and an iodine enhancer in a liquid ether medium (e.g., dioxane), and subjecting the mixture to ultrasonic energy.

Further details of this embodiment, including examples of it, are set forth in a paper which we have written and entitled "Organic Sonochemistry. Sonic Acceleration of the Reformatsky Reaction", pertinent portions of which will now be set forth as part of this specification.

Sonication of reaction mixtures of zinc dust, α-bromo ethylacetate and aldehydes or ketones give 90-100% yields of β-hydroxyesters in 5 to 30 minutes at room temperature. Dioxane solvent and small quantities of iodine are essential to optimum yields and short reaction times. Five aldehydes and three ketones were examined under a variety of conditions. Benzene and ether solvent systems were found to be ineffective. Potassium iodide is a good promoter but increased reaction times (several hours) were required to give the same yields as with iodine. In the absence of $I_2$ and KI starting materials were consumed but no hydroxyesters were formed. In the absence of ultrasound, reactions with no promoters or with only KI gave no hydroxyesters. However, when $I_2$ was used without sonication some products were detected.

The Reformatsky reaction is the most generally applicable procedure for converting aldehydes and ketones to β-hydroxyesters and, consequently, it has been the subject of extensive synthetic and mechanistic study. Significant improvements in the yields of this reaction have been obtained by using freshly prepared zinc powder, a heated column of zinc dust, and a trimethylboratetetrahydrofuran solvent system. Recently we and others have reported significant rate enhancements of chemical reactions carried out in the presence of sonic waves. We are systematically exploring the effects of this phenomenon on chemical reactions and in this paper we describe the beneficial effects that ultrasonic irradiation has on the Reformatsky reaction.

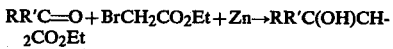

Our results are summarized in the Table. High yields and very short reaction times are the obvious advantages to this technique. Perhaps more important, however, is the elimination of the need to prepare zinc powder by the active metal reduction of anhydrous zinc chloride. Also unnecessary is the use of trimethylborate.

The optimum reaction conditions call for dioxane solvent, a requirement that surpised us because of its tendency to promote enolization under conventional Reformatsky conditions. In our hands, neither ether nor benzene, common Reformatsky solvents, produced high yields even after several hours of sonication. The reason for this selectivity is not obvious but it may be related to the liquid strength of the media.

Earlier studies on promoters demonstrated that small quantities of iodine improved the yields of β-hydroxyesters. This was attributed to the suppression of enolization by iodine which reduced protonation of the zinc intermediate. Our observations were similar. In the presence of the iodine and sonic waves the reaction times were not only reduced to minutes but the yields were essentially quantitative. In the absence of iodine the sonicated mixture of zinc, α-bromoethylacetate and acetophenone reacted slowly (several hours) and gave no addition product. The recovery of ethyl acetate and acetophenone was quantitative. Potassium iodide was also a very effective additive, producing essentially the same yields as the iodine-promoted reactions but on a slower time scale (30 min to 3 h).

While it seems clear that iodine and potassium iodide aid the reaction by suppressing enolization, the increased rates at which zinc reacts with the bromoester suggests that these promoters are also activating the zinc surface. In the absence of sonic waves, iodine-promoted reactions gave modest yields of β-hydroxyesters in 24 h when the molar ratios listed in the Table were used. Very high yields of the β-hydroxyester were obtained after several hours with simply stirring at room temperature when large excesses of zinc and iodine were used. With KI, stirring alone led to no product.

The stoichiometry of the small scale reactions listed in the Table is not optimized. Very likely the same results could be achieved with less iodine than the 1:0.2 carbonyl compound:iodine mole ratio employed. On the larger scale reaction, for example, only a 38.5:1 ratio was needed to give complete reaction in <5 min (Experimental Section).

Experimental Section

The ketones and aldehydes and ethylbromoacetate were used as obtained from commercial sources when the purity was ≧97% as indicated by pmr. Lower purity reagents were distilled or recrystallized to ≧97%. Dioxane was stirred over KOH, distilled from sodium and stored over molecular sieves. Zinc dust was activated by the method of Cava. Iodine and potassium iodide were used as obtained from commercial sources. The sonicator was a Branson Model 220 ultrasound laboratory cleaner (117V, 150W, 50/60 Hz). Proton magnetic resonance spectra were obtained on a Varian Model Em 390. Infrared spectra were obtained from a Perkin Elmer Model 457.

General Procedure for Small Scale Reactions

In a typical experiment, a dry nitrogen-filled 100 ml single-necked round bottom flask was charged with 10 ml of dioxane, 5 mmol of the carbonyl compound, 6 mmol of α-bromoethylacetate, 9 mmol of zinc dust and mmol of iodine. The flask was then partially submerged in the sonicator in a place that produced the greatest agitation of the reaction mixture. The reaction conditions for potassium iodide aided reactions were similar except that relatively larger quantities of zinc (15 mmol) and promoter (4.2 mmol KI) were used. The progress of the reaction, i.e., disappearance of carbonyl substrate, was monitored by pmr.

Product isolation was straightforward. The crude product was poured into an ice-water mixture (100 ml) which was extracted with methylene chloride (2×200 ml) followed by separation and drying of the organic fraction. Removal of the volatiles by flash evaporation and high vacuum (~0.1 torr) gave the desired β-hydroxyester. Each product was characterrized by ir, nmr, and mass spectroscopy. These spectra were compared to those of authentic samples. Yields in the table are based on quantities of isolated product with >95% purity by nmr.

Larger Scale Reformatsky Reaction using n-Butanol and Ethylbromoacetate.

An oven-dried, nitrogen-filled 250 ml single neck round bottom flask was charged with 25 ml of dioxane, 5.4 g (75 mmol) of butanol, 15 g (90 mmol) of ethylbromoacetate, and 8.5 g (130 mmol) of zinc dust. The flask was immersed to the solvent level in the sonicator and iodine was added to the slurry until it became exothermic. This required about 0.5 g. (~2 mmol) of $I_2$. The progress of the reaction was monitored by following the disappearance of the aldehyde proton (triplet, 9.8δ) by pmr. The absorption was gone in <5 min.

The product mixture was poured slowly into an ether-ice slurry with stirring and 1 g of KI was added to remove $I_2$ from the organic layer. This was extracted with ether (2×200 ml) and the combined extracts were dried over $CaCl_2$. Removal of the volatiles by flash evaporation followed by vacuum distillation gave 10.9 g (91%) of ethyl 3-hydroxyheptanoate (bp 75%/0.1 torr) which was identified by pmr and ms.

TABLE

A Comparison of the Yields and Reaction Times for Reformatsky Reactions

| | RR′C(OH)CH₂CO₂Et | | | |
|---|---|---|---|---|
| RR′C=O | Sonically Accelerated | Activated Zinc Powder[2] | (MeO)₃B—THF Solvent[4] | Conventional Method[1,c] |
| 1. R = C₃H₇; R′ = H | 90%; 5 min[a]<br>94%; 2.5 h[b] | 97%; 1 h | 90%; 5 h | 69%, 12 h |
| 2. R = C₇H₁₅; R′ = H | 100%; 5 min[a]<br>100%; 2.5 h[b] | 78%; 1 h | | 80%; 12 h |
| 3. R = C₆H₅; R′ = H | 98%; 5 min[a]<br>98%; 2 h[b] | 98%; 1 h | 95%; 12 h | 61%; 12 h |
| 4. R = 1-naphthyl; R′ = H | 100%; 5 min[a]<br>98%; 2.5 h[b] | | | |
| 5. R = 2-naphthyl; R′ = H | 100%; 5 min[a]<br>100%; 30 min[b] | | | |
| 6. cyclopentanone, | 98%; 30 min[a]<br>97%; 3 h[b] | 97%; 1 h | 87%; 5 h | 50%; 12 h |
| 7. R = R′ = C₃H₇ | 100%; 30 min[a]<br>95%; 3 h[b] | | | |
| 8. R = C₆H₅; R′ = CH₃ | 90%; 30 min[a]<br>96%; 3 h[b] | | | |
| 9. R = R′ = C₆H₅ | 82%; 3 h[a] | | | |

[a]Reactions were run at 25–30° using 1:1.2:1.8:0.20 molar ratios of RR′CO:BrCH₂CO₂Et:Zn:I₂
[b]Same conditions as in a with 1:1.2:3:0.84 molar ratios of RR′CO:BrCH₂CO₂Et:Zn:KI.
[c]Reaction temperature was 80°. The activated zinc powder and (MeO)₃B-THF modifications were run at 25°. The reaction times quoted from references 1, 2 and 4 are probably not optimized but indicate when the reactions were worked up.

Thus ends the pertinent portions from our aforenoted paper entitled "Organic Sonochemistry. Sonic Acceleration of the Reformatsky Reaction".

(4) Making Tetramesityldisilene

The compound formed in this embodiment is noteworthy in that it provides a potential intermediate useful in the formation of semiconducting materials.

The embodiment provides a method of making tetramesityldisilene comprising forming a solution of bis(- mesityl)dichlorosilane in a liquid ether medium (e.g., tetrahydrofuran), with lithium present in the medium, and subjecting the solution to ultrasonic energy.

Further details of this embodiment, including examples of it, are set forth in a paper entitled "Sonochemical and Electrochemical Synthesis of Tetramesityldisilene", which we wrote and which was published heretofore in 1982 in the Journal of the American Chemical Society at Vol. 104, pertinent portions of which will now be set forth as part of this specification:

We have been investigating the effects of sonic waves on heterogeneous reactions, and we have observed some noteworthy rate enhancements. For example, the Wurtz-type coupling of organic halides, RX (R=alkyl, aryl, benzyl, and benzoyl; X=CL, Br, and I), and organometallic chlorides, $R_3MCl$ (R=alkyl, aryl; M=Si, Sn), using lithium wire at room temperature proceeds at a convenient rate only in the presence of sonic waves. We have also found that sonication of a dioxane solution of α, α'-dibromo-o-xylene in the presence of zinc provides easy access to o-xylylene, a reactive intermediate that readily undergoes cycloaddition reactions to activated olefins, and that ultrasound accelerates the Reformatsky reaction requiring neither freshly prepared zinc powders nor acid catalysts. Significant rate enhancements of lithium aluminum hydride reductions of aryl halides, the Barbier reaction, the synthesis of thio amides, and the catalytic reductions of olefins and ketones to hydrocarbons point to considerable potential for sonic waves in synthesis.

In our earlier paper on the sonically accelerated couplings of silicon and tin halides we reported the reaction of lithium with some simple dichlorosilanes to give high yields of cyclopolysilanes:

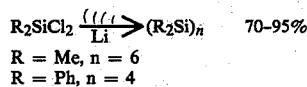

$R_2SiCl_2 \xrightarrow{((\text{l})) \atop Li} (R_2Si)_n$  70-95%

R = Me, n = 6
R = Ph, n = 4

Prompted by the recent discovery by West et al. that the silicon-silicon double bond can be stabilized by four mesityl groups, we extended our study to dimesityldichlorosilane (1).

When a

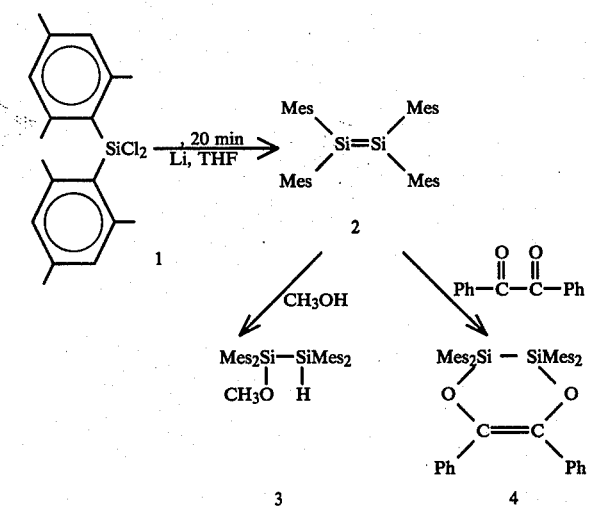

solution of 1 in tetrahydrofuran (THF) was irradiated with ultra-sonic waves in the presence of lithium wire, a yellow color was produced immediately, and within 20 min all of 1 and most of the lithium were consumed. Tetramesityldisilene (2) was isolated from the product mixture in ~ 90% crude yield. Purification by crystallization from hexane gave yellow crystals with spectral features (NMR, IR, mass) essentially identical with those reported by West. When a solution of 2 was treated with methanol we obtained 3 in good yield. This compound was easily purified by column chromatography, and the assigned structure is supported by IR, NMR, and mass spectral data as well as elemental analyses. The addition of 2 to a THF solution of benzil gave a modest yield of the cycloaddition product 4, a compound easily purified and characterized. IR, NMR, and mass spectral data and elemental analyses are consistent with the structure proposed for 4. Analytically pure 3 and 4 were obtained in 72% and 38% yields, respectively, based on the quantity of 1.

In a typical experiment, 1.5 mmol of 1 was added to a 100-mL round-bottomed single-necked flash containing 5 mL of dry THF (distilled from sodium benzophenone ketyl) and ≧3.0 mmol of lithium wire (~¼ in. ×⅛ in. pieces) and partly submerged in a common ultrasound laboratory cleaner (117V, 150W, 50/60 Hz). After 20 min of sonication the yellow-orange product mixture was removed from the vessel by syringe and added to a warm solution of trapping agent.

For the methanol reaction the solution of 2 was added to excess dry methanol at 45° C. and maintained at this temperature for 30 min. The solvent and excess methanol were removed by flash evaporation, and methylene chloride was added. Filtration removed LiCl, and the product 3 was isolated by column chromatography (silica gel, 4:1 v/v pentane: $Ch_2Cl_2$) to give 0.3 g (72%) of 3 as a pale yellow solid, mp 55°–57° C. The benzil quench was carried out in the same fashion by using THF solution of excess benzil at 45° C. The product, 1,2-dipheny-4,4,5,5-tetramesityl-3,6-dioxo-4,5-disila-1-cyclohexene (4) was isolated as pale yellow crystals, mp 67°–68° C., following column chromatography.

Thus ends the pertinent portions from our aforenoted paper entitled "Sonochemical and Electrochemical Synthesis of Tetramesityldisilene.".

(5) Saturating Organic Compounds Having Capability of Reduction at Carbon-Carbon Bonds This embodiment is useful in the manufacture of hydrogenated fats and oils and has a variety of other uses. The capability of the method extends beyond that of simply saturating double and triple bonds and includes saturating isolated and conjugated diene groups, and the opening up of cyclo compounds such as cyclopropanes. The method is useful for the manufacture of pure saturated hydrocarbons, which are especially useful in the drug industry and in others requiring separations. Substantially pure saturated hydrocarbons made by this embodiment simplify the purification procedures employed in chromatography and crystallization separations.

The embodiment provides a method of saturating a broad group of organic compounds, such as those organic compounds having capability of reduction at carbon-carbon bonds. The method itself comprises forming a mixture of an organic compound having capability of reduction at carbon-carbon bonds, and formic acid, in an alcohol medium with palladium-on-carbon present as a catalyst, and subjecting mixture to ultrasonic energy.

Further details of this embodiment, including examples of it, are set forth in a paper which we have written and entitled "Palladium-Catalyzed and Sonically Accelerated Hydrogenations of Olefins Using Formic Acid as a Hydrogen Transfer Agent", pertinent portions of which will now be set forth as part of this specification:

The formic acid/palladium-on-carbon couple was found to be an effective hydrogenating system. Ten olefins including terminal and internal alkenes, a diene, a vinyl ether and an α, β-unsaturated ketone were hydrogenated in high yields at room temperature and atmospheric pressure. Sonication of the reaction mixtures accelerated the reactions as did heating to reflux. Cyclopropylbenzene and diphenyacetylene were reduced quantitatively to n-propylbenzene and bibenzyl respectively.

Formic acid and its derivatives have been used only occasionally to hydrogenate olefins. Lukes and Cervinka reduced a series of tetrahydropyridines in high yields with the $HCO_2H/H_2CO_2K$ couple at 150° C. in 6h. Using a variety of homogeneous precious metal catalysts, Volpin and coworkers found formic acid and its derivatives to be only moderately effective in hydrogenating 1-octene at 100°. In contrast, Blum, Sasson and Iflah were able to use homogeneous ruthenium and iridium catalysts to hydrogenate the double bond in α-β unsaturated ketones quantitatively at 97° with formic acid as the hydrogen donor. More relevant to the work we present here are the report by Nishiguchi and coworkers that supported palladium catalyzed the transfer of hydrogen from formic acid to one of the double bonds in methyl linoleate in 55% and the study by Cortese and Heck demonstrating that atrialkylammonium formate-palladium system will hydrogenate a variety of olefins in 37–93% yields at 100° with reaction times at 1.3 to 48 h.

In this paper we report that, in the presence of palladium on carbon, formic acid is a very efficient hydrogen donor at room temperature and that, in the presence of sonic waves, the rate of hydrogenation is significantly enhanced.

Formic acid was obtained from Matheson, Coleman and Bell (Reagent, ACS) and used without further purification. The palladium catalyst was 10% Pd on activated carbon and was used as obtained from Aldrich (lot #2123 TE). Absolute ethanol was used from stock without further purification. The reagents listed in the table were obtained commercially and used as purchased only if >97% pure as determined by nmr and glc. When needed the reagents were purified by distillation or crystallization to at least 97% purity. Nmr spectra were obtained on a Varian EM-390 spectrometer. Ir spectra were taken on a Perkin-Elmer 257. Product analyses were carried out on a Varian Model 920 Gas Chromatograph.

General Procedure for Small Scale Hydrogenations.

A dry nitrogen-filled 100 ml flask was charged with 6 mmol of olefin, 24 mmol of $HCO_2H$, 0.50g of 10% Pd on carbon (0.47 mmol) and 8 ml of absolute ethanol (Runs 4 and 5 required an additional 8 ml of enzene to dissolve the olefins) and placed in a common laboratory ultrasonic cleaner (Bransonic Model 220). Reactions were run under a nitrogen atmosphere and at ~25°. Both temperatures were maintained at ~25° by means of a 4" muffin fan mounted on the side of the cleaner.

After 1 h of sonication the reaction vessel was removed from the bath, the contents filtered, and the collected solid washed with chloroform or pentane. The combined filtrates were placed on a rotary evaporator and the volatiles removed. Nmr spectra of the residue showed only the hydrogenated product. Spectra of the products obtained from these reactions were identical to those of authentic samples in the Aldrich Library of NMR Spectra. The high level of purity of the products from these reactions was verified by both nmr and glc. Yields were based on the amount of olefin used.

Hydrogenation of trans-Stilbene.

To a dry, nitrogen-filled 250 ml single-necked round-bottom flask fitted with a nitrogen inlet and magnetic stirring bar was added 11.8 g (65.5 mmol) of stilbene, 11 g (240 mmol) formic acid, 5 g of 10% Pd on activated carbon (4.7 mmol Pd), 60 ml of absolute ethanol and 100 ml of dry benzene. The reaction vessel was placed in a sonicator so that the liquid level inside the flask matched that of the bath water and in the location that produced the maximum cavitation in the flask. After 1 h the flask was removed and the contents filtered. The solid was washed with chloroform and the combined filtrates concentrated on a rotary evaporator. The residual soild was recrystallized (ethanol-pentane) to give 11.03g (92.5% yield) of bibenzyl mp 51°–51.5° (lit 52.5) (8).

A variety of unsaturated compounds including cyclic and alicyclic olefins, diene, a vinyl ether and an α-βunsaturated ketone were hydrogenated in very high yields at room temperature using formic acid, 10% palladium on charcoal as the catalyst and ethanol as solvent. Typical olefin: formic acid: catalyst mole ratios were 1:4:0.08. When the reactions were carried out in a common ultrasound laboratory bath cleaner the hydrogenations were complete within one hour. While accurate rate data was not taken, it was observed that when stirring the reagents for 1 h without ultrasound the reactions progressed to ≧70% completion. Two hours was usually enough to give >90% yield. Thus sonic waves, while beneficial, are not necessary. We also investigated the effects of heating without sonication on the hydrogenations of nonene, trans-stilbene and acenaphthene and found quantitative conversion to product when the reaction mixtures were refluxed for 0.25h. Our results with olefins are summarized in the Table.

The reactivity of the formic acid/palladium couple compares very favorably with related systems. For example, α-methylstyrene (Run 6) and the cyclic olefins are essentially quantitatively reduced using formic acid and palladium whereas α-methylstyrene, cyclohexene, and methylcyclohexene are virtually untouched by formic acid in the presence of $(Ph_3P)_3RuHCl(2)$. The facile conversion of mthyloleate to methylstearate (Run 10) contrasts sharply with earlier attempts to hydrogenate unsaturated fatty acid methyl esters with formic acid and the apparently superior donor, indoline(4). Quantitative reduction of benzalacetone (trans-4-phenyl-3-buten-2-one) to 4-phenyl-2-butanone (Run 8) in 1 h at room temperature with $HCO_2H/Pd/C$ compares favorably with the 86% yield obtained in 2.5 h at 100° using the tributylammonium formate-palladium couple and avoids the use of tributylamine.

The results in the Table are for reactions run on 6 mmol of olefin and the yields were computed on the basis of isolated product that was >97% pure by glc and nmr. To demonstrate feasibility of scale-up, 12 g of t-stilbene was hydrogenated and bibenzyl was isolated by crystallization in 93% yield. That formic acid is the exclusive source of hydrogen was shown when t-stilbene was recovered quantitatively from a reaction mixture in which formic acid was omitted.

The high yields, short reaction times, mild conditions and simplicity of work-up are noteworthy features of this system. When the low cost and ease of handling of formic acid and the recyclability of the catalyst are also considered, the HCO₂H-Pd/C couple is potentially very useful as a routine method of hydrogenating olefins.

The donor capabilities of HCO₂H-Pd/C with respect to other organic systems were examined. Thus we found that cyclopropylbenzene is converted to n-propylbenzene quantitatively (no cumene detected) in less

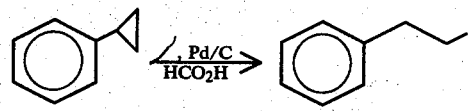

than 0.5 h at room temperature and that diphenylacetylene is reduced to bibenzyl in >98% yield. Diphenylacetylene however, was not hydrogenated at room temperature even with sonication. The reaction mixture must be refluxed for 0.5 h. We are presently exploring the ability of formic acid to donate hydrogen to a variety of functional groups in the presence of other metals and we are evaluating the effects of ultrasound on these reactions.

TABLE

Hydrogenation of Carbon-Carbon Double Bonds by Formic Acid Catalyzed by Palladium on Carbon

| Olefin | Product |
|---|---|
| 1. C₇H₁₅CH=CH₂ᵇ | C₉H₂₀ (100%) |
| 2.  |  (95%) |
| 3.  | 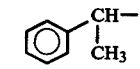 (100%) |
| 4. trans-PhCH=CHPhᵇ | PhCH₂CH₂Ph (100%) |
| 5.  | 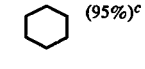 (100%) |

TABLE-continued

Hydrogenation of Carbon-Carbon Double Bonds by Formic Acid Catalyzed by Palladium on Carbon

| Olefin | Product |
|---|---|
| 6.  |  (100%) |
| 7. ⌬ | ⌬ (95%)ᶜ |
| 8. trans-PhC=C—C—CH₃ (H H O) | PhCH₂CH₂CCH₃ (O) (100%) |
| 9. n-C₄H₉OCH=CH₂ | n-C₄H₉OC₂H₅ (93%) |
| 10. methyl 9-octadecenoate | methyl 9-octadecanoate |

ᵃReaction times are not optimized. All runs were sampled after 1 h, found to be complete by nmr and worked up. Pd/C is required. Using activated charcoal only of simply formic acid and olefin gave no reaction with sonication or heating.
ᵇQuantitatively hydrogenated within 0.5 h when refluxed in the absence of sonic waves.
ᶜTrace benzene detected by nmr. In a separate experiment it was shown that when an ethanol solution of cyclohexene was sonicated in the presence of formic acid and palladium on carbon the cyclohexene was converted quantitatively to cycloxene and benzene in a 2:1 ratio respectively.

Thus ends the pertinent portions from our aforenoted paper entitled "Palladium-Catalyzed and Sonically Accelerated Hydrogenations of Olefins Using Formic Acid as a Hydrogen Transfer Agent". In accordance with well-established legal principles, the appended claims are to be construed in a manner embracing equivalents.

That which is claimed is:

1. The method of reducing aryl halides involving nucleophilic substitution of hydrogen for halide on the aryl nucleus, comprising forming a mixture of aryl halide and lithium aluminum hydride in a liquid ether medium, and subjecting the mixture to ultrasonic energy.

2. The method of making cycloaddition products comprising forming a mixture of alpha, alpha'-dibromo-ortho-xylene, zinc powder and a dienophile in a liquid ether medium, and subjecting the mixture to ultrasonic energy.

3. The method of making beta-hydroxyesters comprising forming a mixture of alpha-bromoethylacetate, a carbonyl compound, zinc dust, and an iodine enhancer in a liquid ether medium, and subjecting the mixture to ultrasonic energy.

4. The method of claim 3 wherein the liquid ether medium comprises a cyclic ether.

5. The method of claim 4 wherein the cyclic ether comprises dioxane.

6. The method of making tetramesityldisilene comprising forming a solution of bis(mesityl)dichlorosilane in a liquid ether medium, with lithium present in the medium, and subjecting the solution to ultrasonic energy.

7. The method of saturating organic compounds having capability of reduction at carbon-carbon bonds, comprising forming a mixture of an organic compound having capability of reduction at carbon-carbon bonds, and formic acid, in an alcohol medium with palladium-on-carbon present as a catalyst, and subjecting the mixture to ultrasonic energy.

* * * * *